(12) United States Patent
Thomas et al.

(10) Patent No.: US 12,385,078 B2
(45) Date of Patent: Aug. 12, 2025

(54) BIOELECTRICAL SENSOR DEVICE

(71) Applicant: NOBLIS, INC., Reston, VA (US)

(72) Inventors: Sterling Wells Thomas, Woodbridge, VA (US); Lauren Michelle Leone, Falls Church, VA (US)

(73) Assignee: NOBLIS, INC., Reston, VA (US)

( * ) Notice: Subject to any disclaimer, the term of this patent is extended or adjusted under 35 U.S.C. 154(b) by 888 days.

(21) Appl. No.: 17/119,669

(22) Filed: Dec. 11, 2020

(65) Prior Publication Data

US 2021/0180105 A1 Jun. 17, 2021

Related U.S. Application Data

(60) Provisional application No. 62/946,844, filed on Dec. 11, 2019.

(51) Int. Cl.
| | |
|---|---|
| *C12Q 1/04* | (2006.01) |
| *B01L 3/00* | (2006.01) |
| *B33Y 10/00* | (2015.01) |
| *B33Y 80/00* | (2015.01) |

(52) U.S. Cl.
CPC ............... *C12Q 1/04* (2013.01); *B01L 3/502* (2013.01); *B33Y 10/00* (2014.12); *B33Y 80/00* (2014.12); *B01L 2200/026* (2013.01); *B01L 2200/04* (2013.01); *B01L 2200/12* (2013.01); *B01L 2300/0663* (2013.01); *B01L 2400/0475* (2013.01)

(58) Field of Classification Search
CPC .................................. C12Q 1/04; B01L 3/502
See application file for complete search history.

(56) References Cited

U.S. PATENT DOCUMENTS

2019/0127219 A1* 5/2019 Bengali ............ B01L 3/502707

OTHER PUBLICATIONS

Zhou et al. Ann. Int. Conf. IEEE Eng. Med. Biol. Soc., 2015, 7518-7521 (Year: 2015).*
Ying et al Bio-Design and Manufacturing, 2018, 1.215-224 (Year: 2018).*
Dobozi-King et al J. Biol. Physics and Chemistry, 2005, 5, 3-7 (Year: 2005).*
Yang et al ACS Synthetic Biology, 2015, 4, 815-823 (Year: 2015).*
Ying et al Bio-Design and Manufacturing, 2018, 1.15-224 (Year: 2018).*
Ford Overview of Cellink bioinks, Support portal, 2019. Retrieved from the Internet:<URL: https://cellink.freshdesk.com/support/solutions/articles/35000139917-overview-of-cellink-bioinks> (Year: 2019).*
Zajdel et al. Scientific Reports, 2018, 8, 15293 (Year: 2018).*
Connel et al. PNAS, 2013, 110, 18380-18385 (Year: 2013).*
Liu et al. PNAS, 2017, 114, 2200-2205 (Year: 2017).*
Leang et al. Energy Environ. Sci., 2013, 6, 1901-1908 (Year: 2013).*
Zeng et al. Scientific Reports, 2019, 9, 7275 (Year: 2019).*
Golitsch et al. Biosensors and Bioelectronics, 2013, 47, 285-291 (Year: 2013).*
Bond and Lovley Appl. Environm. Microbiol., 2003, 69, 1548-1555 (Year: 2003).*
Freyman et al. (2019). "3D Printing of Living Bacteria Electrode," Nano Research; 5 pages.
Gootenberg et al. (2017) "Nucleic Acid Detection with CRISPR-Cas13a/C2c2," Science 356: 438-442.
Hajian et al. (2019) "Detection of Unamplified Target Genes via CRISPR—Cas9 Immobilized on a Graphene Field-Effect Transistor," Nat Biomed Eng. 3(6); 24 pages.
Li et al. (2018) "CRISPR-Cas12a-Assisted Nucleic Acid Detection," Cell Discov. 4; 7 pages.
Li et al. (Sep. 15, 2020). "Developing a Population-State Decision System for Intelligently Reprogramming Extracellular Electron Transfer in Shewanella oneidensis," PNAS 117 (37): 23001-23010.
Myhrvold et al. (2018) "Field-Deployable Viral Diagnostics Using CRISPR-Cas13," Science 360 (6384); 19 pages.
Pardee (2016) "Rapid, Low-Cost Detection of Zika Virus Using Programmable Biomolecular Components," Cell 165; 13 pages.
Takhashi et al. "A Low-Cost Paper-Based Synthetic Biology Platform for Analyzing Gut Microbiota and Host Biomarkers," located at https://www.ncbi.nlm.nih.gov/pmc/articles/PMC6104080/ visited on Dec. 11, 2019. (26 pages).
Zajdel (2018) "Pedot:PSS-Based Multilayer Bacterial-Composite Films for Bioelectronics," Sci Rep. 8; 24 pages.
Zeng (2019) "A Novel Bioelectronic Reporter System in Living Cells Tested with a Synthetic Biological Comparator," Scientific Reports 9 (7275); 23 pages.
Zhou (2017) "A Portable Bioelectronic Sensing System (BESSY) for Environmental Deployment Incorporating Differential Microbial Sensing in Miniaturized Reactors," PLoS One 12(9); 21 pages.

* cited by examiner

*Primary Examiner* — Sharmila G Landau
*Assistant Examiner* — Lioubov G Korotchkina
(74) *Attorney, Agent, or Firm* — Morrison & Foerster LLP (57) ABSTRACT

A bioelectrical sensor for detecting one or more pathogens in a fluid sample is provided. The bioelectrical sensor receives a fluid sample comprising one or more pathogens, and detects the one or more pathogens using a series of chemical reactions. The series of chemical reactions include a detection step in which a detector organism detects a pathogen upon coming into contact with and/or to within a certain proximity of the pathogen, and a reporting step in which a reporter organism responds to the detection by generating an electrical signal comprising information about the detected pathogen. The electrical signal may then be transmitted to a computing device, which may identify the pathogen by mapping the generated electrical signal to a known pathogen.

23 Claims, 6 Drawing Sheets

BIOELECTRICAL SENSOR DEVICE

CROSS-REFERENCE TO RELATED APPLICATIONS

This application claims the priority of U.S. Provisional Application No. 62/946,844, filed Dec. 11, 2019, the entire contents of which are incorporated herein by reference.

FIELD OF THE DISCLOSURE

This relates to a bioelectrical sensor device, and, more particularly, to a 3D printed bioelectrical sensor configured to detect one or more organisms (e.g., pathogens) in a fluid sample and respond to detecting the one or more organisms.

BACKGROUND OF THE DISCLOSURE

Biosurveillance, an aspect of biodefense related to the application of physical and analytical methods to detect and counter biological threats, ensures public health. Known biosurveillance methods include deploying aerosol monitors to detect the presence of a pathogen in the air, and employing syndromic surveillance to analyze public health reporting about disease prevalence. Existing cell-free synthetic methods of detection require sample preparation and specialized instrumentation. For example, single molecule detection methods typically require an amplification strategy, such as loop-mediated isothermal amplification (LAMP) or recombinase polymerase amplification (RPA), to achieve desired sensitivity and/or rely on biochemical reactions (e.g., colorimetry) or fluorescence for reporting.

SUMMARY OF THE DISCLOSURE

As described above, existing cell-free synthetic methods of detection require sample preparation and specialized instrumentation. Methods which rely on sample preparation and specialized instrumentation are problematic for several reasons—namely, that they can be very costly, as they can require specific laboratory equipment and/or trained technicians; can be less sensitive; can be difficult to reconfigure to accurately detect a multitude of possible pathogens; and can take a long time to perform. Moreover, the window of time immediately following exposure to one or more pathogens but before signs and symptoms of exposure develop is critical to ensure prophylaxis. More timely and comprehensive threat detection ensures public health and enables new avenues of medical research. Thus, there is a need for improved devices, systems, and methods for quickly, accurately, and flexibly detecting one or more pathogens/toxins in a fluid sample.

Accordingly, provided herein is a low-cost, high-trust, sensitive, massively multiplexed, reconfigurable, and fieldable bioelectrical sensor for biosurveillance. The provided bioelectrical sensor, systems which integrate the provided bioelectrical sensor, and methods to manufacture the provided bioelectrical sensor may address one or more of the needs explained above by quickly, accurately, and flexibly detecting known and potentially engineered signature nucleic acid sequences of human pathogens and host biomarkers of infection in blood, urine, saliva, or other bodily fluids to inform medical support decisions.

In some embodiments, a bioelectrical sensor system is provided for identifying one or more pathogens/toxins in a fluid sample. The system may include a loading port, a pump, a substrate, a bioelectrical sensor disposed on the substrate, a signal channel, and a computing device. In some embodiments, the bioelectrical sensor may comprise a reaction chamber and one or more reaction elements disposed within the reaction chamber.

In some embodiments, the loading port may be configured to allow for a fluid sample (e.g., blood, urine, saliva, or other bodily fluids) to be loaded into the system by flowing into the system via the loading port. In some embodiments, the system may be a closed system and the pump may be configured to direct fluid flow through the system. In some embodiments, the reaction chamber may be configured to receive and emit fluid flow such that the system may detect organisms (e.g., pathogens) in fluid that flows through the reaction chamber.

In some embodiments, the reaction chamber may have one or more reaction elements disposed therein, wherein a reaction element may be any component configured to respond to the presence of an organism in the fluid flowing through the reaction chamber. Thus, when a pathogen in the fluid sample comes into contact with a reaction element inside the reaction chamber, the reaction element may be configured to detect the presence of the pathogen and to cause the system to generate a signal indicating the presence of the pathogen. In some embodiments, a reaction element may comprise an organism, such as an organism disposed within a bioink from which the reaction element is formed, may be configured to detect a target pathogen, and may be configured to respond to the detection of the target pathogen by generating an electrical signal. The signal channel may include a wire configured to transmit the electrical signal from the first reaction element to the computing device. In some embodiments, the computing device may be configured to identify the first target pathogen based on the electrical signal received. In some embodiments, the computing device may be configured to, upon identifying the first target pathogen, generate and store and/or transmit an automated alert comprising information about the first target pathogen.

In some embodiments, the reaction chamber may comprise a plurality of reaction elements, each of which may be configured to independently detect associated organisms (e.g., pathogens) and responsively generate electrical signals. In some embodiments, multiple reaction elements in a single reaction chamber may be configured to detect the same organism/pathogen; in some embodiments, different reaction elements in a single reaction chamber may be configured to independently detect different organisms/pathogens.

In some embodiments, the bioelectrical sensor may be 3D printed. In some embodiments, a method of manufacturing a 3D printed bioelectrical sensor may comprise fabricating a base layer of the reaction chamber using a bioink and/or printing the reaction elements using a bioink. In some embodiments, the base layer of the reaction chamber may be fabricated using a material other than a bioink (e.g., a plastic, glass, or metal). In some embodiments, the base layer of the reaction chamber and/or the reaction elements may printed using a bioprinter. In some embodiments, the base layer of the reaction chamber and the first reaction element may be printed using the same bioprinter using different printer heads, without needing to replace cartridges in the printer heads or pause the printing process. In some embodiments, the method may comprise curing the base layer of the reaction chamber using photo and/or chemical curing and/or curing the reaction elements using photo and/or chemical curing. In some embodiments, the reaction elements may be inserted into the reaction chamber after the base layer of the reaction chamber has cured. In some embodiments, after the reaction elements have been inserted into the reaction chamber, a top layer of the reaction chamber may be fabricated using the same material used to fabricate the base layer, or a different material (e.g., a different bioink or a different material other than a bioink) and cured using photo and/or chemical curing.

As explained herein, the bioelectrical sensor, methods of manufacturing a 3D printed bioelectrical sensor, and the bioelectrical sensor system may be used to quickly and accurately identify one or more pathogens in a fluid sample. By using the bioelectrical sensor, which can detect tens or hundreds of natural pathogens and their potentially engineered variants, the labor, equipment, and time required to identify one or more pathogens in a fluid sample may be decreased. Furthermore, accuracy and testing sensitivity may be improved, as well as the ability to robustly and/or rapidly reconfigure the biosensor to identify alternative pathogens.

In some embodiments, a bioelectrical sensor for detecting one or more pathogens in a fluid sample is provided, the sensor comprising: a reaction chamber configured to receive and emit fluid; and a first reaction element disposed within the reaction chamber, wherein the first reaction element comprises a first organism configured to detect a first target pathogen, and wherein the first reaction element is configured to respond to the detection of the first target pathogen by generating an electrical signal.

In some embodiments of the bioelectrical sensor, the reaction chamber comprises a plurality of layers, wherein one or more of the layers comprise GelMA C bioink.

In some embodiments of the bioelectrical sensor, the first reaction element is configured to be contacted by the fluid as the fluid flows through reaction chamber.

In some embodiments of the bioelectrical sensor, the first reaction element comprises a first layer, the first layer comprising the first organism configured to detect a first target pathogen.

In some embodiments of the bioelectrical sensor, the first organism is *Shewanella oneidensis*.

In some embodiments of the bioelectrical sensor, the first reaction element comprises a first set of outer layers, wherein the first set of outer layers comprises the first organism configured to detect a first target pathogen.

In some embodiments of the bioelectrical sensor, the first reaction element comprises a second organism, the second organism configured to respond to the detection of the first target pathogen by generating an electrical signal.

In some embodiments of the bioelectrical sensor, the second organism is synthetic.

In some embodiments of the bioelectrical sensor, the first reaction element comprises an inner region disposed between the first set of outer layers.

In some embodiments of the bioelectrical sensor, the inner region comprises the second organism.

In some embodiments of the bioelectrical sensor, the first reaction element comprises a set of intermediate layers disposed between the first set of outer layers and the inner region.

In some embodiments of the bioelectrical sensor, the set of intermediate layers comprises a chemical that fuels a chemical reaction in the second organism.

In some embodiments of the bioelectrical sensor, a second reaction element is disposed within the reaction chamber.

In some embodiments of the bioelectrical sensor, one or more of the first reaction element and the second reaction element comprise pluronics.

In some embodiments of the bioelectrical sensor, the second reaction element comprises a third organism configured to detect a second target pathogen, wherein the second reaction element is configured to respond to the detection of the second target pathogen by generating a second electrical signal.

In some embodiments of the bioelectrical sensor, the first reaction element and the second reaction element are spaced apart from one another in the reaction chamber such that the fluid comes into contact with both the first reaction element and the second reaction element as it flows through the reaction chamber.

In some embodiments of the bioelectrical sensor, the bioelectrical sensor is configured to be attachable to and detachable from a bioelectrical sensor device, such that the biolelectrical sensor is in fluid communication with the bioelectrical senor device when attached thereto.

In some embodiments of the bioelectrical sensor, the first organism is synthetic.

In some embodiments, a bioelectrical sensor system for identifying one or more pathogens in a fluid sample is provided, the system comprising: a loading port for loading a fluid sample into the system; a pump for directing fluid flow through the system; a substrate; a bioelectrical sensor disposed on the substrate, the sensor comprising: a reaction chamber configured to receive and emit fluid; and a first reaction element disposed within the reaction chamber, wherein the first reaction element comprises a first organism configured to detect a first target pathogen, and wherein the first reaction element is configured to respond to the detection of the first target pathogen by generating an electrical signal; a signal channel configured to transmit the generated electrical signal; and a computing device configured to receive from the signal channel the generated electrical signal and identify, based at least in part on receiving the generated electrical signal from the signal channel, the first pathogen in the fluid sample.

In some embodiments of the bioelectrical sensor system, the first organism is configured to generate a voltage upon detecting the first target pathogen.

In some embodiments of the bioelectrical sensor system, the first reaction element is configured to respond to the detection of the first target pathogen by generating an electrical signal based on the generated voltage.

In some embodiments of the bioelectrical sensor system, the pump is a peristaltic pump, wherein the pump is configured to generate cross-directional fluid flow through the reaction chamber.

In some embodiments of the bioelectrical sensor system, the bioelectrical sensor is removable from the substrate, wherein the substrate is reusable.

In some embodiments of the bioelectrical sensor system, the signal channel comprises a wire configured to pass the generated electrical signal from the first reaction element to the computing device.

In some embodiments of the bioelectrical sensor system, the computing device is disposed on the substrate.

In some embodiments of the bioelectrical sensor system, the computing device is configured to identify the first pathogen in the fluid sample by mapping the received signal to the first pathogen.

In some embodiments of the bioelectrical sensor system, the computing device is configured to, upon identifying the first pathogen in the fluid sample, generate an automated alert comprising information about the first pathogen.

In some embodiments of the bioelectrical sensor system, the system is configured to provide the identification of the first pathogen in the fluid sample in less than 15 minutes from a time at which the fluid sample is loaded into the system to a time at which the first pathogen in the fluid sample is identified.

In some embodiments, a method of manufacturing a bioelectrical sensor for detecting one or more pathogens in a fluid sample is provided, the method comprising: printing a base layer of a reaction chamber using a 3D printing material, wherein the reaction chamber is configured to receive and emit fluid flow; curing the base layer of the reaction chamber using one or more of photo curing and chemical curing; printing a first reaction element using a first bioink, wherein the first bioink comprises a first organism configured to detect a first target pathogen; and curing the first reaction element using one or more of photo curing and chemical curing.

In some embodiments of the method of manufacture, the 3D printing material is a second bioink, wherein the second bioink is different from the first bioink.

In some embodiments of the method of manufacture, printing the reaction chamber base layer is performed using a first printer head of a bioprinter, wherein the first printer head is configured to deposit a 3D printing material; and printing the first reaction element is performed using a second printer head of the bioprinter, wherein the second printer head is configured to deposit a first bioink.

In some embodiments of the method of manufacture, the first reaction element comprises: a set of outer layers that comprise the first organism; and a set of intermediate layers that comprise a second organism and are disposed between the set of outer layers.

In some embodiments of the method of manufacture, printing the first reaction element comprises: forming the set of outer layers by depositing the first bioink using the second printer head; and forming the set of intermediate layers using a third printer head of the bioprinter.

In some embodiments of the method of manufacture, the third printer head is configured to deposit a third bioink, wherein the third bioink is different than the first bioink.

In some embodiments of the method of manufacture, the method comprises: printing a top layer of the reaction chamber using the 3D printing material; and curing the top layer of the reaction chamber using one or more of photo curing and chemical curing.

In some embodiments of the method of manufacture, curing the first reaction element is performed before inserting the first reaction element into the reaction chamber.

In some embodiments of the method of manufacture, printing the first reaction element comprises printing the first reaction element directly onto the reaction chamber base layer.

In some embodiments of the method of manufacture, curing the base layer and curing the first reaction element are performed as a single curing process.

In some embodiments of the method of manufacture, curing the base layer and curing the first reaction element are performed as separate curing processes.

In some embodiments, a method of detecting a pathogen using a bioelectrical sensor is provided, the method comprising: causing a fluid sample comprising the pathogen to flow into a reaction chamber of the bioelectrical sensor, wherein the reaction chamber comprises a first reaction element comprising a first organism configured to detect the pathogen, and wherein the first reaction element is configured to respond to the detection of the pathogen by generating an electrical signal; receiving, at a computing device, the generated electrical signal; and identifying, based at least in part on receiving the generated electrical signal, the pathogen in the fluid sample.

BRIEF DESCRIPTION OF THE DRAWINGS

Various embodiments are described with reference to the accompanying figures, in which.

DETAILED DESCRIPTION OF THE DISCLOSURE

Described herein is a bioelectrical sensor, bioelectrical sensor systems, methods of use of bioelectrical sensors, and methods of manufacturing bioelectrical sensors. In particular, provided are systems and methods for receiving a fluid sample containing one or more pathogens, detecting the one or more pathogens in the fluid sample using a bioelectrical sensor, identifying the one or more pathogens, and generating an alert or other indication comprising information about the one or more pathogens. Bioelectrical sensors such as those disclosed herein may enable users to more quickly, accurately, and robustly identify one or more pathogens and perform medical countermeasures to prevent or mitigate the onset of disease. The bioelectrical sensor enables quicker, more accurate, and more robust identification of one or more pathogens by independently and simultaneously detecting up to tens or hundreds of known pathogens and their potentially engineered variants, and by being rapidly reconfigurable.

Figure 1A:
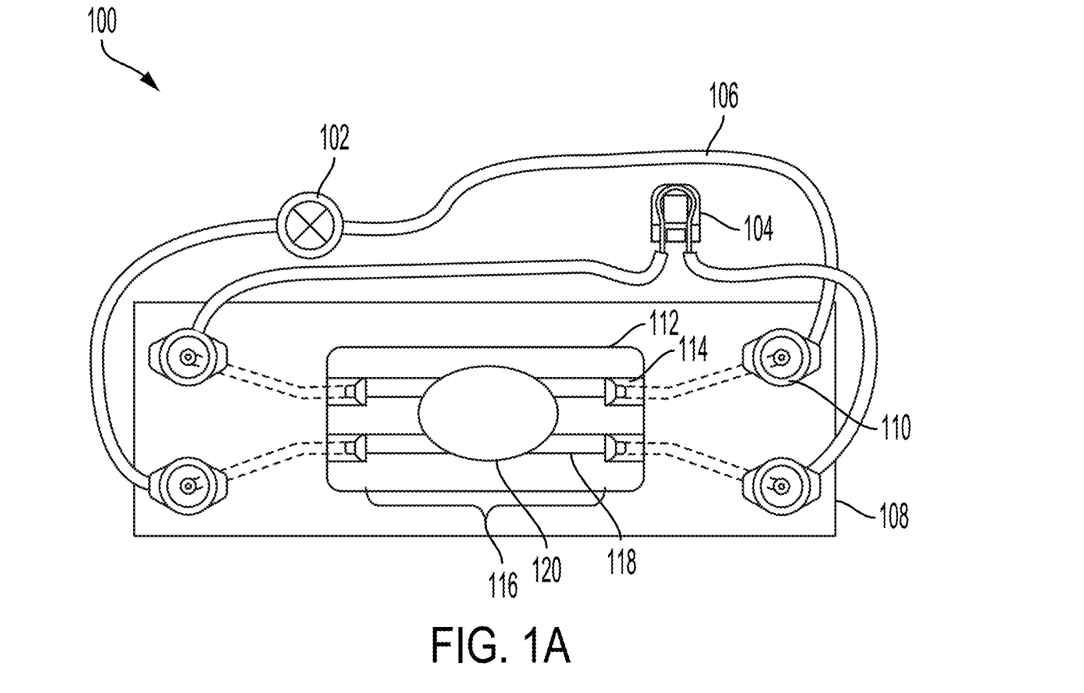
FIG. 1A depicts a top-down view of a bioelectrical sensor system, according to some embodiments.

FIG. 1A depicts a bioelectrical sensor system 100, according to some embodiments. Bioelectrical sensor system 100 comprises a loading port 102; a pump 104; tubing 106; a body 108; a first connector 110; a region 112; a second connector 114; and a bioelectrical sensor 116, which comprises a flow channel 118 and a reaction chamber 120. In some embodiments, loading port 102 may be any port, inlet, valve, or the like configured to receive flow of a fluid sample. In some embodiments, pump 104 may be a peristaltic pump. In some embodiments, pump 104 may provide a flow rate ranging from about 5 µL/min to 500 µL/min, or in some embodiments from about 10 µL/min to about 100

μL/min. In some embodiments, pump 104 may be configured to transport fluid from loading port 102 to bioelectrical sensor 116 via tubing 106. In some embodiments, tubing 106 may comprise any suitable material including, for example, plastic, polymer, and/or glass.

In some embodiments, system 100 may be configured to cause the fluid sample to flow (e.g., from inlet port 102) into and through reaction chamber 120, such that reaction elements inside reaction chamber 120 may detect and report the presence of pathogens in the fluid sample. In some embodiments, bioelectrical sensor system 100 may be a closed system and pump 104 may be configured to generate cross-directional flow across the bioelectrical sensor 116 to avoid fluid stagnation. In some embodiments, tubing 106 may comprise a plurality of pieces of tubing to transport fluid through bioelectrical sensor 116 in a cyclical manner. In some embodiments, each of the plurality of pieces of tubing may be connected to a first connector 110 disposed within a body 108. In some embodiments, each connector of the set of first connectors 110 may be any suitable connector configured to connect tubing 106 to body 108; for example, tubing 106 may comprise a luer connector disposed on its end, and the first connector may be a stopcock, a luer adapter, a female/female luer lock connector, or a male/male luer lock connector. In some embodiments, body 108 may comprise four first connectors 110 such that each is located at or near a corner of the body. In some embodiments, body 108 fits within a 36 mm×85 mm×19 mm bounding box.

In some embodiments, after passing through the first connector 110 and into the body 108, the fluid may flow to a region 112 of the body 108. In some embodiments, the region 112 may be an inner cavity of the body 108. The inner cavity region may be configured such that different reaction chambers may be inserted into and connected to body 108. Thus, body 108 may be reused with single-use reaction chambers. In some embodiments, region 112 may comprise a length of less than or equal to 26 mm and a width of less than or equal to 13 mm. In some embodiments, region 112 may comprise a substrate, which may comprise glass. In some embodiments, the fluid may flow to region 112 of the body 108 by passing through second connector 114. In some embodiments, body 108 may comprise four second connectors 114 such that each receives fluid flow emanating from and/or emits fluid flow to one first connector and is located at or near a corner of region 112. In some embodiments, bioelectrical sensor 116 may be disposed in region 112 of the body.

In some embodiments, bioelectrical sensor 116 may be disposed on a substrate within region 112. In some embodiments, the substrate is reusable; for example, bioelectrical sensor 116 may be removed from the substrate and the substrate may be autoclaved (e.g., at 121° C. for 15 minutes) before being reused. In some embodiments, the fluid which is in region 112 flows to bioelectrical sensor 116 via flow channel 118. In some embodiments, flow channel 118 may be 1 mm above a bottom of region 112. In some embodiments, the fluid which is in region 112 may flow to the bioelectrical sensor via a plurality of flow channels. In some embodiments, bioelectrical sensor system 100 may comprise four flow channels 118 such that each receives fluid flow emanating from and/or emits fluid flow to one second connector. In some embodiments, two of the four flow channels 118 may be located on a side of the reaction chamber 120, approximately 6 mm apart from one another, and two of the four flow channels 118 may be located on an opposite side of the reaction chamber 120, approximately 6 mm apart from one another.

In some embodiments, reaction chamber 120 may comprise a plurality of ports for receiving and emitting fluid. In some embodiments, reaction chamber 120 may comprise one port for each flow channel 118. In some embodiments, once fluid flows through reaction chamber 120, it may flow out via one or more flow channels 118, and may cycle through the system again.

Figure 1B:
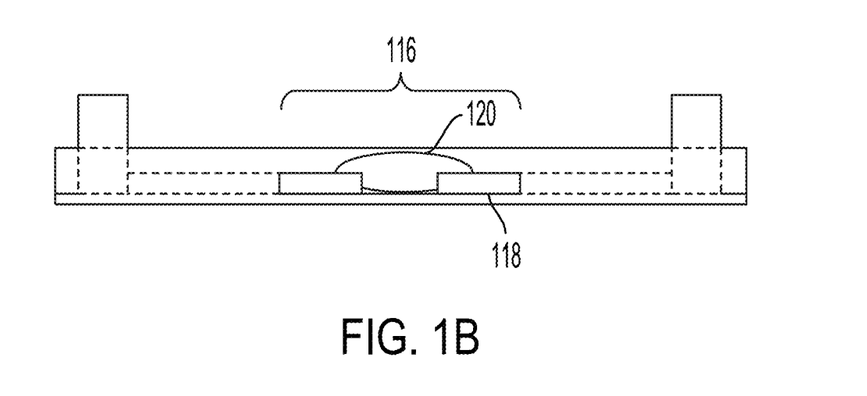
FIG. 1B depicts a side-view of a reaction chamber and flow channels of the bioelectrical sensor system depicted in FIG. 1A, according to some embodiments.

FIG. 1B depicts a side view of bioelectrical sensor 116, showing two flow channels 118 and reaction chamber 120. In some embodiments, one or more of the flow channels 118 may overlap a portion of the reaction chamber 120, as shown. In some embodiments, one or more of the flow channels 118 may not overlap a portion of the reaction chamber 120, and may instead be configured to extend only as far as needed to transmit fluid to and from the reaction chamber 120.

In some embodiments, system 100 may be configured to provide different flow patterns and different directions of flow, which may for example be configured in consideration of optimizing a throughput flow rate and causing fluid samples to flow through reaction chamber 120 in such a manner that the fluid sample comes into contact with all reaction elements disposed therein.

Figure 2:
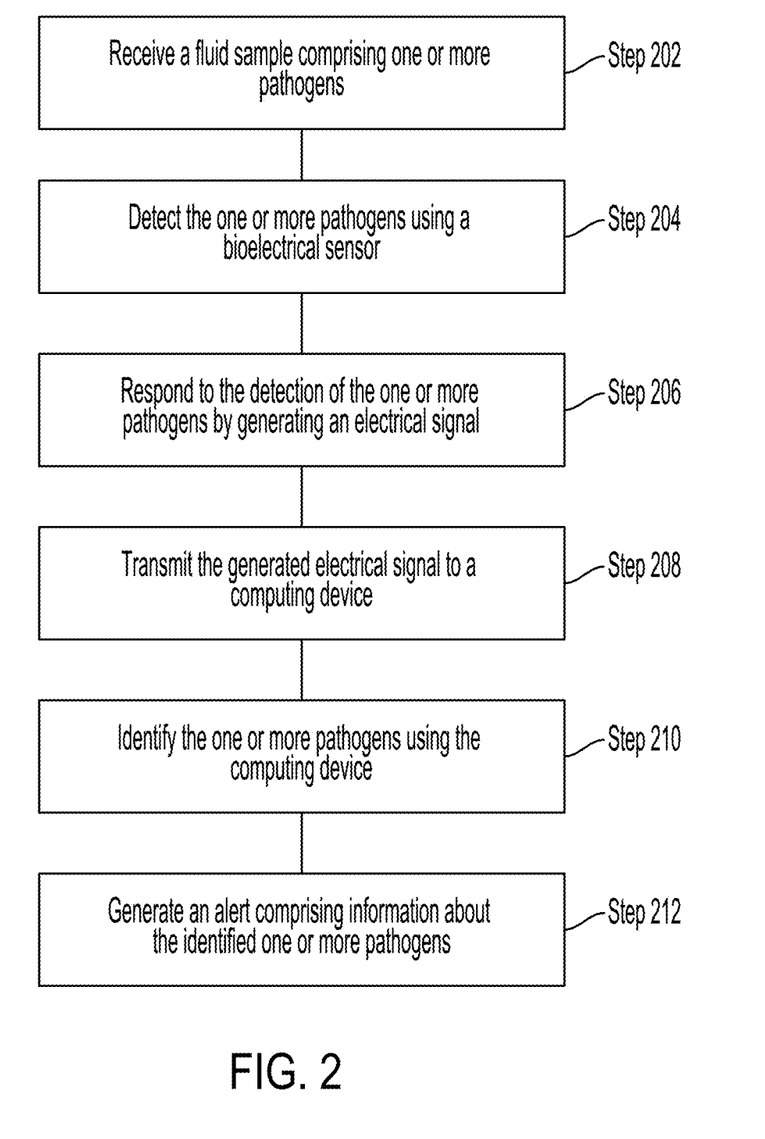
FIG. 2 depicts a flowchart of a method of use of a bioelectrical sensor system, according to some embodiments.

FIG. 2 depicts a flowchart of a method of use of a bioelectrical sensor system (e.g., bioelectrical sensor system 100 of FIG. 1A), according to some embodiments. As shown, FIG. 2 depicts a method by which a bioelectrical sensor system identifies one or more pathogens in a fluid sample by detecting the one or more pathogens using a bioelectrical sensor.

At block 202, in some embodiments, a fluid sample may be loaded into a loading port (e.g., loading port 102 of FIG. 1A) of the bioelectrical sensor system. In some embodiments, the fluid sample may comprise one or more pathogens. In some embodiments, fluid from the fluid sample may be transported from the loading port to a bioelectrical sensor (e.g., bioelectrical sensor 116 of FIG. 1A) of the bioelectrical sensor system (e.g., via pump 104, tubing 106, reaction vessel 108, and flow channel 118 as described with respect to FIG. 1A).

At block 204, in some embodiments, the bioelectrical sensor may detect one or more pathogens in the fluid. In some embodiments, one or more reaction elements of the bioelectrical sensor are configured to detect the one or more pathogens. In some embodiments, the one or more reaction elements may be configured to generate a voltage upon detecting the one or more pathogens. For example, upon coming into contact with and/or to within a certain proximity of a pathogen, one or more organisms embedded in a reaction element may undergo a chemical reaction in which ions (e.g., metal ions) are released. The release of ions causes a change in voltage in a system (e.g., bioelectrical sensor system 100 of FIG. 1) which comprises the bioelectrical sensor.

At block 206, in some embodiments, the one or more reaction elements of the bioelectrical sensor may be configured to respond to the detection of the one or more pathogens by generating an electrical signal based at least in part on the generated voltage. For example, upon a change of voltage in a system (e.g., bioelectrical sensor system 100 of FIG. 1) which comprises the bioelectrical sensor, one or more organisms embedded in a reaction element may undergo a chemical reaction in which ions (e.g., metal ions) are reduced. The reduction of ions causes a change in an electric potential in the system, which may be used to generate an electrical signal. In some embodiments, a plurality of reaction elements may simultaneously each generate separate electrical signals if each detects a known pathogen it is configured to detect.

At block 208, in some embodiments, the bioelectrical sensor may be configured to transmit the one or more generated electrical signals to a computing device. In some embodiments, the bioelectrical sensor may transmit the generated one or more electrical signals to the computing device via a signal channel. In some embodiments, the signal channel may include a wire connected on one end to the bioelectrical sensor (e.g., to a reaction element therein) and on the other end to the computing device.

At block 210, in some embodiments, the computing device may be configured to identify the one or more pathogens in the fluid. In some embodiments, the computing device may be a miniature computer, such as an Arduino or a Raspberry Pi. In some embodiments, the computing device may be disposed on a substrate on which the bioelectrical sensor is also disposed. In some embodiments, the computing device may be provided remotely from the bioelectrical sensor. In some embodiments, the computing device may be configured to identify the one or more pathogens in the fluid by mapping a received electrical signal to a known pathogen. In some embodiments, the computing device may map the received electrical signal to a known pathogen by associating an address of a reaction element from which the electrical signal originated to a known pathogen that the reaction element is configured to detect. In some embodiments, the computing device may store the associations in a database (e.g., store an association for each reaction element so that a signal produced from a reaction element is mapped to a known pathogen). In some embodiments, the computing device may simultaneously map a plurality of electrical signals, for example one generated by each of a plurality of reaction elements that detect respective pathogens in the fluid, to respective known pathogens.

At block 212, in some embodiments, the computing device may be configured to generate an alert comprising information about the identified one or more pathogens. In some embodiments, the alert may be automatically generated upon identification of the identified one or more pathogens. In some embodiments, the computing device may comprise algorithms and/or analytics tools to aid interpretation of assay results and generate the alert. In some embodiments, the alert may include an indication regarding the severity or significance of the one or more pathogens, recommended action to be taken, and/or other relevant information based on the identification. In some embodiments, the alert may be stored and/or transmitted to a system or person from whom the fluid sample was taken and/or a medical monitor (e.g., a medical professional).

Figure 3A:
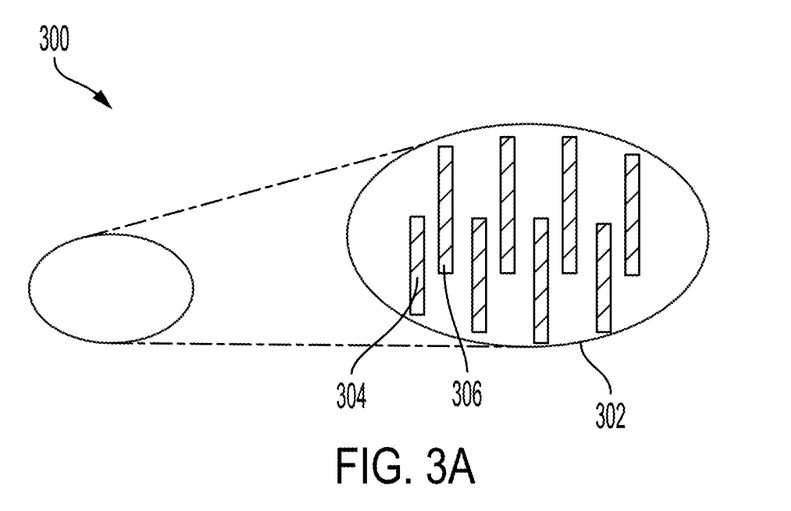
FIG. 3A depicts a top-down view of a cross-section inside a reaction chamber of a bioelectrical sensor, according to some embodiments.

FIG. 3A depicts a top-down view of a cross-section inside a reaction chamber 302 (e.g., reaction chamber 120 of FIG. 1A) of a bioelectrical sensor 300 (e.g., bioelectrical sensor 116 of FIG. 1A), according to some embodiments. In some embodiments, bioelectrical sensor 300 comprises a first reaction element 304 and a second reaction element 306. The reaction chamber may be a housing in which one or more chemical reactions take place, such that the input to the reaction chamber may be a fluid sample comprising one or more pathogens and the output emanating from the reaction chamber may be electrical signals generated by reaction elements therein, the electrical signals indicating that the one or more pathogens were detected. In some embodiments, the reaction chamber comprises one or more reaction elements, at which the chemical reactions may occur (e.g., a reaction element may comprise a detector organism and/or a reporter organism, such that upon being contacted by the fluid sample, the detector and reporter may undergo chemical reactions to detect a pathogen in the fluid sample).

In some embodiments, detector organisms and/or reporter organisms used in the systems or methods disclosed herein may include electroactive bacteria and/or an organism capable of extracellular electron transfer. In some embodiments, *Shewanella oneidensis* and/or *Shewanella putrefaciens* may function as a detector organism and/or as a reporter organism. In some embodiments, *Geobacter metallireducens, Geobacter sulfurreducens,* and/or *Clostridium butyricum* may function as a reporter organism (as these species can generate electrical differentials although they may not react to the presence of a pathogen/toxin). In some embodiments, *Saccharomyces cerevisiae* may function as a detector organism (as this species may react to the presence of a pathogen/toxin although it may not generate any electrical differential).

In some embodiments, a cross-section of the reaction chamber may be ovular. In some embodiments, a cross-section of one or more of the first reaction element and the second reaction element may be rectangular. In some embodiments, a height of the reaction chamber (extending in a direction that runs out of the page in the overhead view of FIG. 3A) is less than or equal to 30 mm, 25 mm, 20 mm, 10 mm, or 5 mm at its tallest point. In some embodiments, a width of the reaction chamber (extending in a direction that runs perpendicular to a longitudinal direction of the reaction elements) (e.g., the up and down direction in the overhead view of FIG. 3A) is less than or equal to 100 mm, 50 mm, 25 mm, 10 mm, or 5 mm at its widest point. In some embodiments, the width is less than or equal to 26 mm at its widest point. In some embodiments, a length of the reaction chamber (extending in a direction that runs parallel to the longitudinal direction of the reaction elements) (e.g., the left and right direction in the overhead view of FIG. 3A) is less or equal to 100 mm, 50 mm, 25 mm, 10 mm, or 5 mm at its longest point. In some embodiments, the length is less than or equal to 26 mm at its longest point. In some embodiments, the reaction chamber may be longer than it is wide.

Reaction chamber 302 is shown to comprise eight reaction elements in the example of FIG. 3. In some embodiments, reaction chamber 302 may comprise any suitable number of reaction elements. In some embodiments, reaction chamber 302 may include greater than or equal to 10 reaction elements, 50 reaction elements, 100 reaction elements, 500 reaction elements, or 1000 reaction elements.

In some embodiments, a plurality of reaction elements disposed in reaction chamber 302 may each be configured to detect the same organism/pathogen. In some embodiments, a plurality of reaction elements disposed in reaction chamber 302 may each be configured to detect different organisms/pathogens.

In some embodiments, reaction elements may be disposed within reaction chamber 302 in any suitable spatial arrangement such that fluid flowing through reaction chamber 302 may come into contact with one or more (or all) of the reaction elements. In some embodiments, reaction elements may be disposed such that they extend width-wise across the entirety of a width of reaction chamber 302 or part of a width of reaction chamber 302, and fluid may be configured to flow lengthwise through reaction chamber 302 (e.g., into an inlet at one lengthwise end and out of an outlet at an opposite lengthwise end) such that the fluid passes by the reaction elements that extend width-wise across the chamber. In some embodiments, reaction elements may extend across an entire height of reaction chamber 302, while in some embodiments they may extend less than the entire height. In some embodiments, reaction elements may extend across an entire length of reaction chamber 302, while in some embodiments they may extend less than the entire length. In some embodiments, reaction elements may be arranged within reaction chamber 302 in such a manner as to cause fluid flowing through reaction chamber 302 to follow a flow pattern dictated by the reaction elements, such as a serpentine flow pattern caused by the staggered arrangement of reaction elements shown in FIG. 3A.

In some embodiments, the first reaction element 304 and the second reaction element 306 may comprise semi-permeable membranes. In some embodiments, the first reaction element 304 and the second reaction element 306 are positioned in the reaction chamber 302 such that the first reaction element and the second reaction element are staggered relative to each other. This staggered arrangement may minimize fluid stagnation in the reaction chamber and may enable fluid to optimally contact both the first reaction element and the second reaction element. It may be advantageous for fluid to contact both the first contact element and the second contact element so that each may undergo an independent reaction and may be configured to detect a different pathogen. In some embodiments, first reaction element 304 extends such that one end touches an inner side wall of reaction chamber 302 and second reaction element 306 extends such that neither end touches an inner side wall of reaction chamber 304. The arrangement of reaction elements in the reaction chamber may be modified such that none of the reaction elements abut the reaction chamber side walls, all of the reaction elements abut the reaction chamber side walls, or some of the reaction elements abut the reaction chamber side walls, as shown.

Figure 3B:
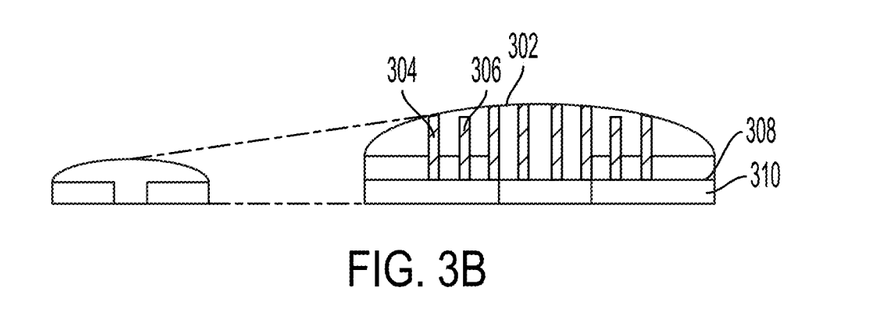
FIG. 3B depicts a side-view of a cross-section inside the reaction chamber of the bioelectrical sensor depicted in FIG. 3A, according to some embodiments.

FIG. 3B depicts a side-view of a cross-section inside reaction chamber 302 of bioelectrical sensor 300, according to some embodiments. In some embodiments, reaction chamber 302 comprises a signal channel 308 configured to transmit electrical signals from one or more of the reaction elements to a computer configured to receive and process the electrical signals. In some embodiments, signal channel 308 is disposed in reaction chamber 302 adjacent to (e.g., underneath) the first reaction element and the second reaction element. In some embodiments, flow channel 310 (e.g., flow channel 118 of FIG. 1A) may overlap a portion of reaction chamber 302, as discussed above with respect to FIG. 1B.

Figure 4:
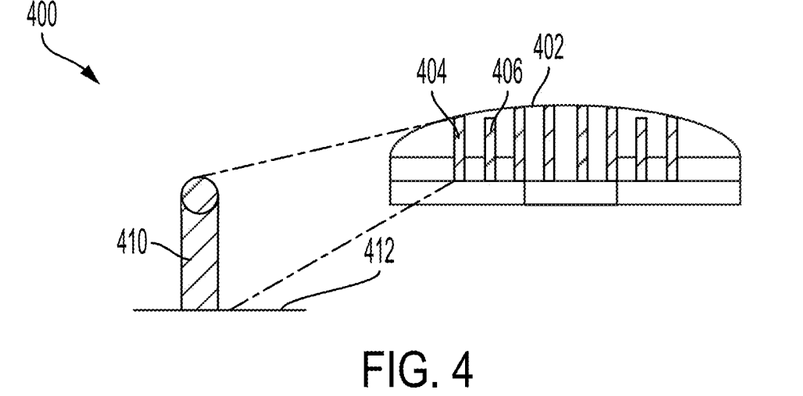
FIG. 4 depicts one embodiment of a reaction element of a bioelectrical sensor.

FIG. 4 depicts one embodiment of a reaction element of a bioelectrical sensor 400 (e.g., bioelectrical sensor 116 of FIG. 1A). This embodiment shows a configuration in which a reaction element comprises a single layer that comprises a first organism which serves as both a detector and a reporter to detect and identify a first target pathogen. The first organism may, upon coming into contact with and/or to within a certain proximity of the first target pathogen, detect the first target pathogen by generating a voltage. The first organism may then report the detection of the first target pathogen by generating an electrical signal based at least in part on the generated voltage. Bioelectrical sensor system 400 comprises reaction chamber 402, first reaction element 404, and second reaction element 406. As shown in the zoomed-in portion of FIG. 4, first reaction element 404 may comprise a reaction element body 410. In some embodiments, first reaction element 404 and/or second reaction element 406 may be configured to be contacted by fluid as it passes from one end of reaction chamber 402 to the other end of reaction chamber 402. In some embodiments, reaction element body 410 of first reaction element 404 may comprise a first layer. In some embodiments, the first layer may extend across an entire width (measured in a direction extending from left to right when viewed from the side as shown in FIG. 4) of the reaction element.

In some embodiments, the first layer may comprise a first organism (e.g., an organism embedded in a bioink from which the layer is formed) configured to detect a first target pathogen. In some embodiments, the first organism may be embedded in the first layer. In some embodiments, the first organism may function as a detector in that, upon coming into contact with and/or to within a certain proximity of the first target pathogen, the first organism may generate a voltage. In some embodiments, the first organism may be configured to generate a voltage by triggering the release of ions (e.g., metal ions), which causes a voltage change in the bioelectrical sensor. In some embodiments, the first target organism may additionally respond to the detection of the first target pathogen by generating an electrical signal. In some embodiments, the first organism may generate the electrical signal by reducing the released ions and changing an electric potential in the bioelectrical sensor. In some embodiments, the first organism may be a synthetic organism. In some embodiments, the first organism may be *Shewanella oneidensis*. In these embodiments, the *Shewanella oneidensis* may be engineered so that it can both detect and respond to detecting the first target pathogen. For example, a phage (e.g., a virus that infects and replicates within bacteria and archaea) that detects a toxin released by a pathogen and increases the production of ions (e.g., to cause a voltage change at a level that is detectable by a voltmeter) in response to the detection may be inserted into the *Shewanella oneidensis*. The *Shewanella oneidensis* may then reduce the released ions to cause a change in electric potential and generate an electrical signal. In some embodiments, the generated electrical signal may be transmitted from bioelectrical sensor 400 via signal channel 412 (e.g., as discussed in block 202 of FIG. 2); a segment of signal channel 412 is shown in FIG. 4.

Figure 5:
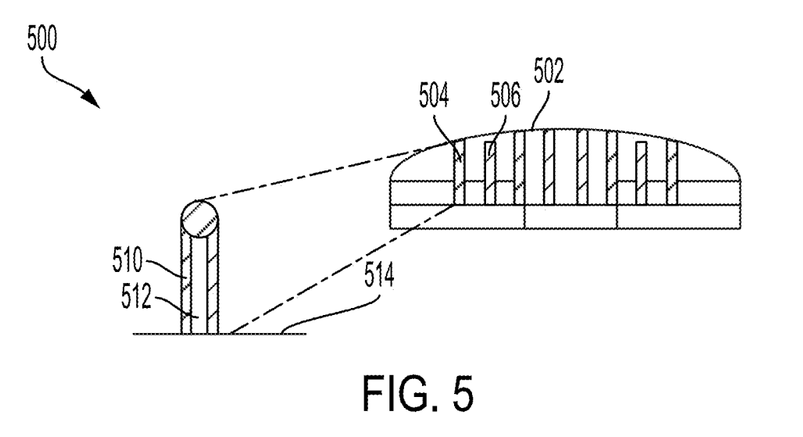
FIG. 5 depicts one alternative embodiment of a reaction element of a bioelectrical sensor.

FIG. 5 depicts one alternative embodiment of a reaction element of a bioelectrical sensor 500 (e.g., bioelectrical sensor 116 of FIG. 1A). This embodiment shows a configuration in which a reaction element comprises multiple layers, for example a set of outer layers that comprise a first organism (e.g., a detector) and an inner region that comprises a second organism (e.g., a reporter). The first organism may, upon coming into contact with and/or to within a certain proximity of the first target pathogen, detect the first target pathogen by generating a voltage. The second organism may then report the detection of the first target pathogen by generating an electrical signal based at least in part on the generated voltage. Bioelectrical sensor system 500 comprises reaction chamber 502, first reaction element 504, and second reaction element 506. As shown in the zoomed-in portion of FIG. 5, first reaction element 504 may comprise a first set of outer layers 510 and an inner layer 512. In some embodiments, inner layer 512 may be hollow (e.g., such that fluid may flow therein) or may be solid. In some embodiments, inner layer 512 has a width (measured in a direction extending from left to right when viewed from the side as shown in FIG. 5) equal to approximately one-third to half of a width of first reaction element 504. The width of the inner layer may be configured to be sufficient such that the inner layer can support the overall structure of reaction element 504 if either or both of the layers of the set of outer layers 510 are removed. In some embodiments, the first set of outer layers 510 may comprise two layers, one on either side of the first reaction element 504 (e.g., such that one layer is on the left-most side of first reaction element 504 and the other layer is on the right-most side of first reaction element 504 when viewed from the side as shown in FIG. 5).

In some embodiments, each layer of the first set of outer layers 510 may comprise a first organism configured to detect a first target pathogen. In some embodiments, only one layer of the first set of outer layers 510 may comprise the first organism. In some embodiments, the first organism may be embedded in the first set of outer layers 510. In some embodiments, the first organism may function as a detector in that, upon coming into contact with and/or to within a certain proximity of the first target pathogen, the first organism may generate a voltage (e.g., by triggering the release of ions, as discussed above with respect to FIG. 4).

In some embodiments, the released ions travel from the first set of outer layers 510 to the inner layer 512. In some embodiments, inner layer 512 may comprise a second organism that may respond to the generation of voltage by generating an electrical signal (e.g., by reducing the ions and changing an electric potential, as discussed above with respect to FIG. 4). In some embodiments, the second organism may flow freely in the inner layer 512. In some embodiments, the second organism or may be embedded in the inner layer 512. In some embodiments, the first organism and/or the second organism may be synthetic organisms. In some embodiments of the configuration shown in FIG. 5, the second organism may be *Shewanella oneidensis* and the first organism may be an organism different than *Shewanella oneidensis* (or vice versa).

In some embodiments, the first organism may comprise a chemical (e.g., carbon) that enables the second organism to react. For example, in an embodiment in which the second organism is *Shewanella oneidensis,* the second organism uses a carbon source to reduce ions released by the first organism. In some embodiments, the chemical may be embedded into an extracellular matrix of the first organism. In these embodiments, the carbon source and the ions may emanate from the same regions of first reaction element 504 (e.g., from an organism comprised in the first set of outer layers 510) and travel to inner reaction layer 512 in which the second organism may be disposed.

In some embodiments, the generated electrical signal may be transmitted from bioelectrical sensor 500 via signal channel 514 (e.g., as discussed in block 202 of FIG. 2); a segment of signal channel 514 is shown in FIG. 5.

Figure 6:
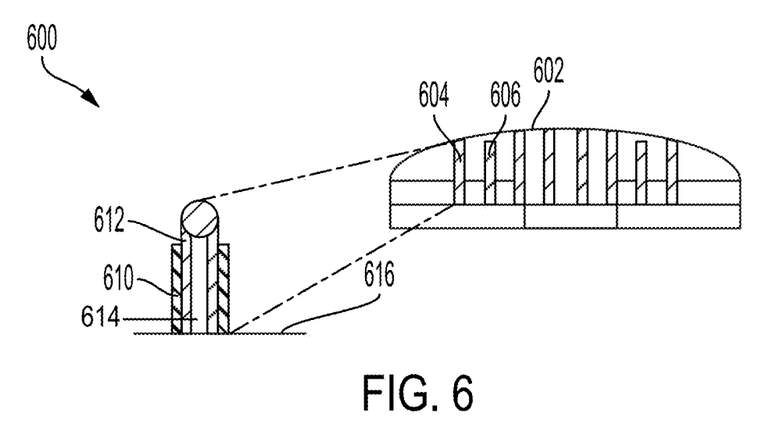
FIG. 6 depicts another alternative embodiment of a reaction element of a bioelectrical sensor.

FIG. 6 depicts another alternative embodiment of a reaction element of a bioelectrical sensor 600 (e.g., bioelectrical sensor 116 of FIG. 1A). This embodiment shows a configuration in which a reaction element comprises multiple layers, for example a first set of outer layers that comprise a first organism (e.g., a detector), an inner region that comprises a second organism (e.g., a reporter), and a first set of intermediate layers that comprise a chemical (e.g., carbon) which enables the second organism to chemically react upon detection of a pathogen. The first organism may, upon coming into contact with and/or to within a certain proximity of the first target pathogen, detect the first target pathogen by generating a voltage. The chemical may constantly or intermittently be emitted from the set of intermediate layers to the inner layer comprising the second organism to fuel a chemical reaction in the second organism (e.g., to keep the second organism alive). The second organism may report the detection of the first target pathogen by generating an electrical signal based at least in part on the generated voltage. Bioelectrical sensor system 600 comprises reaction chamber 602, first reaction element 604, and second reaction element 606. As shown in the zoomed-in portion of FIG. 6, first reaction element 604 may comprise a set of outer layers 610, a set of intermediate layers 612, and an inner layer 614. In some embodiments, inner layer 614 has a width (measured in a direction extending from left to right when viewed from the side as shown in FIG. 6) equal to approximately half of a width of first reaction element 604. In some embodiments, the first set of outer layers 610 may comprise two layers, one on either side of the first reaction element 604 (e.g., such that one layer is on the left side of first reaction element 604 and the other layer is on the right side of first reaction element 604 when viewed from the side as shown in FIG. 6).

In some embodiments, each layer of the first set of outer layers 610 may comprise a first organism configured to detect a first target pathogen. In some embodiments, only one layer of the first set of outer layers 610 may comprise the first organism. In some embodiments, the first organism may be embedded in the first set of outer layers 610. In some embodiments, the set of intermediate layers 612 may comprise two layers, one on either side of the first reaction element 604 (e.g., such that one layer is on the left side of first reaction element 604 and the other layer is on the right side of first reaction element 604 when viewed from the side as shown in FIG. 6). In some embodiments, the set of intermediate layers 612 is disposed between the set of outer layers 610 and the inner layer 614.

In some embodiments, upon detecting the first target pathogen, the first organism may be configured to generate a voltage (e.g., by triggering the release of ions, as discussed above with respect to FIG. 4). In some embodiments, inner layer 614 may comprise a second organism that reacts to the detection of the first target pathogen by the first organism. In some embodiments, the second organism may be flow freely in the inner layer 614 and/or may be embedded in the inner layer 614.

In some embodiments, each layer of the set of intermediate layers 612 may comprise a chemical that enables the second organism to react. In some embodiments, only one layer of the first set of outer layers 610 may comprise the chemical. For example, in an embodiment in which the second organism is *Shewanella oneidensis,* the second organism uses a carbon source to reduce ions (e.g., metal ions) released by the first organism. If carbon cannot be embedded (or is not embedded) into the extracellular matrix of the first organism, then it may be embedded into the set of intermediate layers 612. In these embodiments, the carbon source and the ions may emanate from distinct regions of first reaction element 604 (e.g., the carbon source may emanate from a chemical comprised in the set of intermediate layers 612 and the ions may emanate from an organism comprised in the first set of outer layers 610) and travel to inner layer 614 in which the second organism may be disposed.

In some embodiments, the second organism may respond to the generation of voltage by generating an electrical signal (e.g., by reducing the ions and changing an electric potential, as discussed above with respect to FIG. 4). In some embodiments, the first organism, the chemical, and/or the second organism may be synthetic organisms. In some embodiments, the generated electrical signal may be transmitted from bioelectrical sensor 600 via signal channel 616 (e.g., as discussed in block 202 of FIG. 2); a segment of signal channel 616 is shown in FIG. 6.

As explained above, a first reaction element may be configured to comprise only a first layer; a first set of outer layers and an inner layer; or a first set of outer layers, a set of intermediate layers, and an inner layer. The first reaction element may be modified to comprise three or more sets of outer layers, or may be modified to comprise two or more layers, each of which comprises a different organism and/or chemical. Additionally, a second reaction element may be configured according to any of these configurations.

In some embodiments, the bioelectrical sensor may comprise a second reaction element, as described above. In some embodiments, the second reaction element (e.g., second reaction element 406 of FIG. 4) may comprise a third organism configured to detect a second target pathogen and/or a fourth organism configured to generate an electrical signal. In some embodiments, the second target pathogen is different from the first target pathogen. Thus, the system may be configured to simultaneously detect and report distinct pathogens, which may for example be detected in a mixed sample. In some embodiments, the simultaneous detection and reporting by the first reaction element and the second reaction element are independent biological processes. In some embodiments, detection and/or reporting by the first reaction element and/or the second reaction element may be a destructive process, such that the first reaction element and/or the second reaction element may be used only one time. In these embodiments, even if the first reaction element has been used to detect and report a first target pathogen, the bioelectrical sensor may still be used to detect and report a second target pathogen (or vice versa).

As explained herein, the first reaction element and the second reaction element may be configured to detect different target pathogens. A third reaction element may be configured to detect a third target pathogen, distinct from both the first target pathogen and the second target pathogen, or a third reaction element may be configured to detect either the first target pathogen or the second target pathogen (for example to increase the reliability of testing results). Further, a bioelectrical sensor may comprise four or more reaction elements, each of which may be configured to detect a distinct target pathogen.

In some embodiments, the bioelectric sensor is disposable, such that when it becomes ineffective or a user no longer wishes to use it, the bioelectrical sensor may be removed and replaced by a new bioelectrical sensor. In some embodiments, the new bioelectrical sensor may be configured to detect the same target pathogens compared to the used bioelectrical sensor, or the new bioelectrical sensor may be configured to detect one or more different target pathogens (e.g., by substituting one reaction element with another, by adding an additional reaction element, and/or by removing a reaction element) compared to the used bioelectrical sensor.

Figure 7:
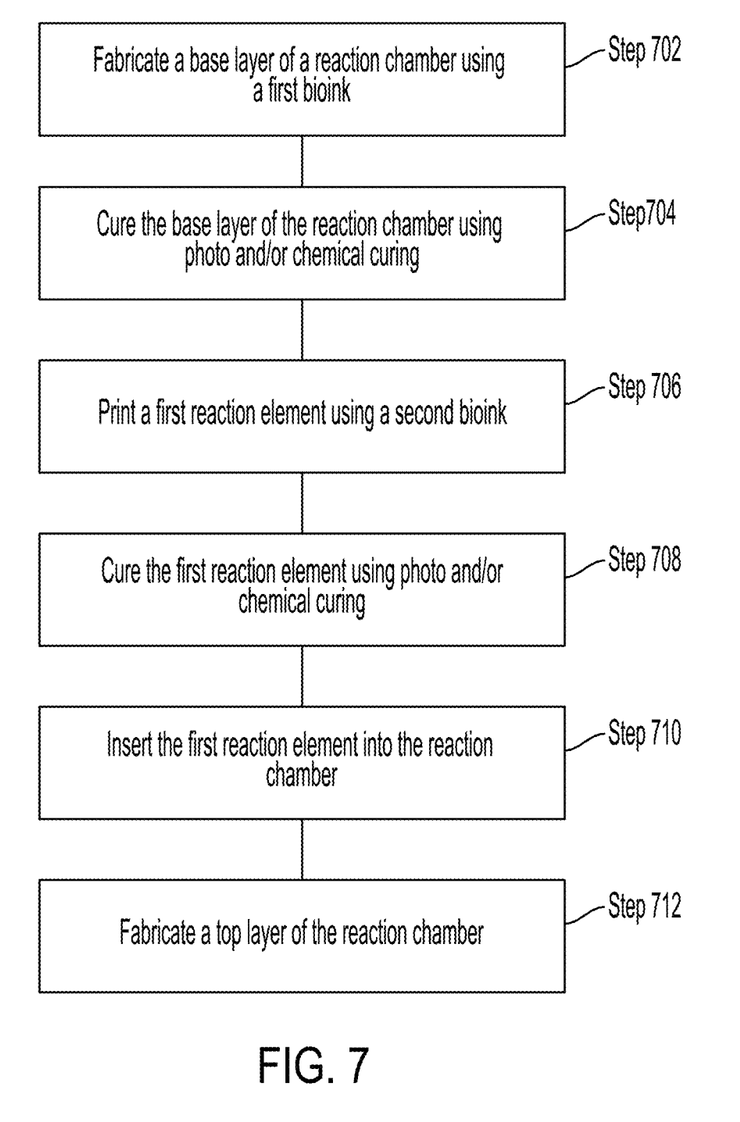
FIG. 7 depicts a flowchart of a method of manufacturing a 3D printed bioelectrical sensor, according to some embodiments.

FIG. 7 depicts a flowchart of a method of manufacturing a 3D printed bioelectrical sensor (e.g., bioelectrical sensor 300 of FIGS. 3A and 3B), according to some embodiments. As shown, FIG. 7 depicts a method by which a bioelectrical sensor is 3D printed.

At block 702, in some embodiments, a base layer of a reaction chamber (e.g., reaction chamber 120 shown in FIGS. 1A and 1B) is fabricated. In some embodiments, the base layer may be fabricated by 3D printing the base layer. In some embodiments, the base layer may be 3D printed using a bioprinter (e.g., the CELLINK INKREDIBLE+ bioprinter or the CELLINK BIOX bioprinter). The term bioprinter may refer to a 3D printer configured to print 3D constructs comprising one or more cell types; moreover, a bioprinter may offer a sterile internal environment for the one or more cell types. In some embodiments, the base layer may be biologically inert, and may be 3D printed using any 3D printing material (e.g., PLA, ABS, or PET). In some embodiments, the base layer may be 3D printed using a first bioink, for example GELMA C bioink. The term bioink may refer to a biomaterial suitable for bioprinting with cells; the bioink provides a temporary or permanent support to the cells while the cells produce an extracellular matrix. Bioinks may be based on biopolymers, such as collagen, gelatin, hyaluronan, silk, alginate, nanocellulose, or the like. Bioinks may provide an aqueous 3D environment which comprise biologically relevant chemical and physical signals similar to those present in a natural extracellular matrix environment. In some embodiments, the base layer may be 3D printed at a temperature of within +/−5° C. of 130° C., 120° C., 110° C., 100° C., 90° C., 80° C., or 70° C., 60° C., 50° C., 40° C., or 30° C., such that the base layer is initially liquid when printing.

In some embodiments, for example if the base layer comprises GELMA C bioink, instead of 3D printing the base layer, the base layer may be fabricated by spreading heated GELMA C bioink (e.g., heated to about 37° C. or more via an incubator or bean heater) over a substrate (e.g., substrate 112 of FIG. 1A) according to a desired conformation.

At block 704, in some embodiments, the base layer of the reaction chamber may be cured. In some embodiments, curing the base layer may comprise crosslinking the base layer with UV light (e.g., photo crosslinking at wavelengths of about 365 nm and/or about 405 nm) and/or crosslinking the base layer with calcium chloride solution. In some embodiments, it may be advantageous to cure the base layer only with calcium chloride solution (e.g., the UV curing process may result in unwanted shrinkage of the base layer and/or may damage cells if embedded in the bioink of the base layer). In some embodiments, the base layer may be cooled (e.g., to about room temperature) to induce gelation of the base layer. In some embodiments, other layers of the reaction chamber may be disposed on the base layer.

At block 706, in some embodiments, a first reaction element (e.g., first reaction element 304 of FIGS. 3A and 3B) is fabricated. In some embodiments, the first reaction element may be fabricated by 3D printing the first reaction element. In some embodiments, the first reaction element may be 3D printed using a bioprinter (e.g., the CELLINK INKREDIBLE+ bioprinter or the CELLINK BIOX bioprinter). In some embodiments, the first reaction element may be 3D printed using a second bioink, for example pluronics. In some embodiments, the second bioink may be biologically active (e.g., may comprise one or more organisms, such as the detector and/or the reporter). In contrast, as discussed at block 702, the first bioink may be biologically inert. In some embodiments, the first reaction element may be 3D printed at a chilled temperature (e.g., less than room temperature, for example a temperature of within +/−5° C. of 20° C., 10° C., 0° C., −10° C., −20° C., −30° C., −40° C., −50° C., −60° C., −70° C., −80° C., or −100° C.), such that the first reaction element is initially liquid when printing. The printing temperature may depend on the particular bioink used to print the first reaction element. In some embodiments, the first reaction element is printed onto the base layer of the reaction chamber.

In some embodiments, a bioprinter comprising a plurality of printer heads may be used to print the base layer of the reaction chamber using the first bioink and the first reaction element using the second bioink. In these embodiments, a first printer head may be configured to deposit the first bioink used to print the base layer of the reaction chamber and a second printer head may be configured to deposit the second bioink used to print the first reaction element. Using the same bioprinter to print the base layer of the reaction chamber and the first reaction element may be advantageous at least to avoid replacing cartridges in the printer heads and/or pausing the printing process. In some embodiments, the base layer of the reaction chamber and the first reaction element may be printed using different bioprinters. Using different bioprinters to print the base layer of the reaction chamber and the first reaction element may be advantageous at least to avoid manufacturing inefficiencies which would be caused if one of the reaction chamber and the first reaction element print quicker than the other and/or to maintain greater flexibility over the printing process by more precisely setting the bioprinter.

In some embodiments, as discussed above with respect to FIGS. 5 and 6, the first reaction element may comprise a plurality of organisms and/or chemicals. In these embodiments, each of the organisms and/or chemicals may be printed using a different bioink (e.g., the first set of outer layers 610 may be printed using the second bioink and the set of intermediate layers 612 may be printed using a third bioink). In some embodiments, a bioprinter comprising a plurality of printer heads may be used to print using the different bioinks (e.g., a second printer head configured to deposit the second bioink may be used to print the first set of outer layers 610 and a third printer head configured to deposit the third bionk may be used to print the set of intermediate layers 612).

In some embodiments, as discussed above with respect to FIG. 4, the reaction chamber may comprise a plurality of reaction elements, each of which may be configured to detect and respond to a different target pathogen and may comprise one or more unique organisms. In some embodiments, each of the reaction elements may be printed using the same bioprinter (e.g., using an additional printer head of the bioprinter to print each unique organism). Using the same bioprinter to print the plurality of reaction elements may be advantageous at least to avoid replacing cartridges in the printer heads and/or pausing the printing process. In some embodiments, each reaction element may be printed using a different bioprinter. Using a different bioprinter to print the plurality of reaction elements may be advantageous at least to maintain greater flexibility to rapidly reconfigure one or more of the reaction elements comprised in the reaction chamber.

At block 708, in some embodiments, the first reaction element may be cured. In some embodiments, curing the first reaction element may comprise crosslinking the first reaction element with UV light (e.g., photo crosslinking at wavelengths of 365 nm and/or 405 nm) and/or crosslinking the base layer with calcium chloride solution. In some embodiments, it may be advantageous to cure the first reaction element only with calcium chloride solution (e.g., the UV curing process may damage the one or more organisms embedded in the bioink of the first reaction element). In some embodiments, the first reaction element may be warmed to solidify, for example to a temperature of at least 10° C., 20° C., 30° C., 32° C., 35° C., 40° C., or 50° C. In some embodiments, the cured and solidified first reaction element may be inserted into the reaction chamber. Additional reaction elements may be similarly crosslinked and solidified, and all reaction elements may be crosslinked and solidified simultaneously. In some embodiments, the reaction elements may be cured simultaneously to the base layer (which may be cured as discussed at block 704), such that curing the base layer and curing the reaction element are performed as a single curing process.

At block 710, in some embodiments, the first reaction element may be inserted into the reaction chamber. In some embodiments, the first reaction element may be inserted into the reaction chamber after one or both of the reaction element and reaction chamber have been cured (e.g., cured separately from one another). In some embodiments, the first reaction element may be inserted into the reaction chamber by printing the first reaction element directly onto the base layer of the reaction chamber. In these embodiments, it may be advantageous to chemically cure the base layer of the reaction chamber, as UV curing may damage any organisms comprised within the first reaction element. In some embodiments, it may be advantageous to cure the base layer before inserting the reaction elements. In some embodiments, the first reaction element may be inserted manually or via a machine for enhanced accuracy and precision. Additional reaction elements may be similarly inserted into the reaction chamber.

At block 712, a top layer of the reaction chamber may be fabricated and/or attached to the reaction chamber. In some embodiments, the top layer is fabricated using a wax casting process, such that a hollow reaction chamber with an internal cavity is produced. In some embodiments, the top layer may be provided as a preformed lid that is attached to the reaction chamber after the reaction elements have been inserted. One of ordinary skill in the art will recognize that many other methods of fabricating and/or attaching the top layer of the reaction chamber may be employed.

In some embodiments, a bioelectrical sensor (e.g., bioelectrical sensor 116 of FIG. 1) may be configured to be a wearable device. In some embodiments of the wearable configuration, the bioelectrical sensor may be configured to screen bodily fluids incrementally. In some embodiments of the wearable configuration, the bioelectrical sensor may comprise an electronic locator device (e.g., a GPS device) to locate the wearer of the device. In some embodiments, the bioelectrical sensor may be configured to be a point-of-need device. Both the wearable and point-of-need embodiments of the bioelectrical sensor may be configured to simultaneously detect hundreds of known and potentially engineered pathogens. Both the wearable and the point-of-need embodiments may be configured to detect and identify known and potentially engineered pathogens in less than 15 minutes. This rapid detection and identification enables identification before symptoms develop and enables rapid prophylaxis.

In some embodiments, the 15 minute timeframe may include an amount of time during which fluid comprising one or more pathogens flows through a system (e.g., bioelectrical sensor system 100 of FIG. 1), an amount of time during which the fluid sits in a reaction chamber (e.g., reaction chamber 120 of FIG. 1), an amount of time during which a detector and/or a reporter react to detect a pathogen in the fluid sample, and/or an amount of time during which a computing device processes one or more received electrical signals to identify the one or more pathogens. In some embodiments, as described above, multiple pathogens may be simultaneously detected, such that the detection of one pathogen does not serve as a rate-limiting step for the detection of another pathogen. Thus, the 15 minute timeframe may refer to a total end-to-end processing time to receive a fluid sample comprising one or more pathogens and identify the one or more pathogens comprised within the fluid sample.

Figure 8:
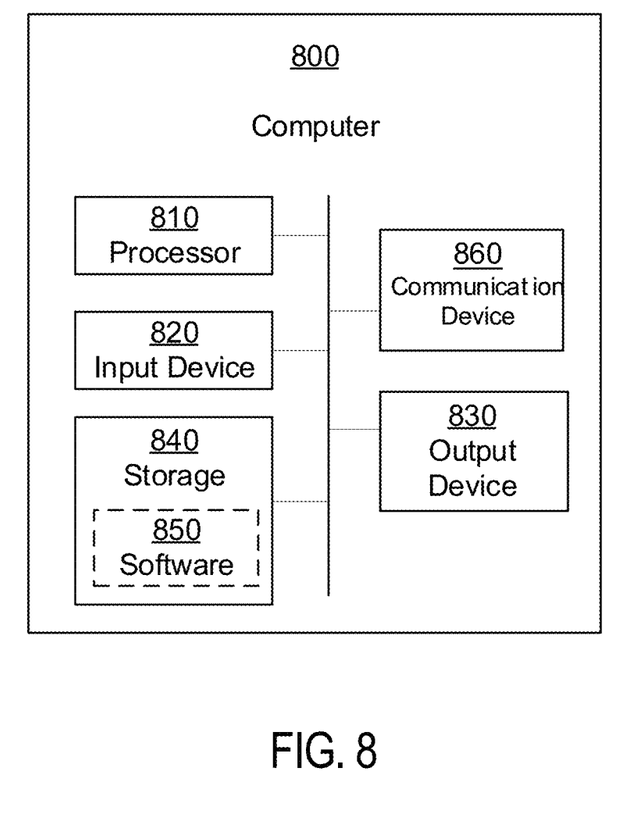
FIG. 8 depicts a computing device, according to some embodiments.

FIG. 8 illustrates an example of a computer, according to some embodiments. Computer 800 can be a component of a bioelectrical sensor system according to the systems and methods described above, such as system 100 of FIG. 1. In some embodiments, computer 800 may execute a method for identifying one or more pathogens in a fluid sample, for example by performing analysis of signals received from a bioelectrical sensor and/or by sending control signals to a bioelectrical sensor device to control flow of fluid through the device.

Computer 800 can be a host computer connected to a network. Computer 800 can be a client computer or a server. As shown in FIG. 8, computer 800 can be any suitable type of microprocessor-based device, such as a personal computer, workstation, server, or handheld computing device, such as a phone or tablet. The computer can include, for example, one or more of processor 810, input device 820, output device 830, storage 840, and communication device 860. Input device 820 and output device 830 can correspond to those described above and can either be connectable or integrated with the computer.

Input device 820 can be any suitable device that provides input, such as a touch screen or monitor, keyboard, mouse, or voice-recognition device. Output device 830 can be any suitable device that provides an output, such as a touch screen, monitor, printer, disk drive, or speaker.

Storage 840 can be any suitable device that provides storage, such as an electrical, magnetic, or optical memory, including a random access memory (RAM), cache, hard drive, CD-ROM drive, tape drive, or removable storage disk. Communication device 860 can include any suitable device capable of transmitting and receiving signals over a network, such as a network interface chip or card. The components of the computer can be connected in any suitable manner, such as via a physical bus or wirelessly. Storage 840 can be a non-transitory computer-readable storage medium comprising one or more programs, which, when executed by one or more processors, such as processor 810, cause the one or more processors to execute methods described herein.

Software 850, which can be stored in storage 840 and executed by processor 810, can include, for example, the programming that embodies the functionality of the present disclosure (e.g., as embodied in the systems, computers, servers, and/or devices as described above). In some embodiments, software 850 can include a combination of servers such as application servers and database servers.

Software 850 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include but is not limited to, an electronic, magnetic, optical, electromagnetic, or infrared wired or wireless propagation medium.

Computer 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 800 can implement any operating system suitable for operating on the network. Software 850 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A bioelectrical sensor for detecting one or more pathogens in a fluid sample, the sensor comprising:
a reaction chamber to receive and emit fluid; and
a reaction element disposed within the reaction chamber, wherein the reaction element comprises a first organism of a first species to detect a target pathogen, and comprises a second organism of a second species to generate an electrical signal, wherein the first organism detects the target pathogen by generating a voltage, wherein the second organism responds to the detecting of the target pathogen by generating the electrical signal based at least in part on the voltage generated by the first organism, wherein the reaction element comprises a set of outer layers and an inner region disposed between the set of outer layers, the inner region is a hollow region and the second organism flows freely in a fluid in the inner region, and the reaction element allows ions released in response to the detection of the target pathogen by the first organism to travel from the set of outer layers to the inner region.

2. The bioelectrical sensor of claim 1, wherein the reaction chamber comprises a plurality of layers, and wherein one or more of the layers comprise bioink.

3. The bioelectrical sensor of claim 1, wherein the reaction element is to be contacted by the fluid as the fluid flows through the reaction chamber.

4. The bioelectrical sensor of claim 1, wherein the reaction element comprises a first layer of the set of outer layers, the first layer comprising the first organism to detect a target pathogen.

5. The bioelectrical sensor of claim 1, wherein the first organism is *Shewanella oneidensis*.

6. The bioelectrical sensor of claim 1, wherein the set of outer layers comprises the first organism.

7. The bioelectric sensor of claim 1, wherein the second organism is synthetic.

8. The bioelectrical sensor of claim 1, wherein the reaction element comprises a set of intermediate layers disposed between the set of outer layers and the inner region.

9. The bioelectrical sensor of claim 8, wherein the set of intermediate layers comprises a chemical that fuels a chemical reaction in the second organism.

10. The bioelectrical sensor of claim 1, wherein a second reaction element is disposed within the reaction chamber.

11. The bioelectrical sensor of claim 10, wherein one or more of the reaction element and the second reaction element comprise pluronics.

12. The bioelectrical sensor of claim 10, wherein the second reaction element comprises a third organism to detect a second target pathogen, and wherein the second reaction element responds to the detection of the second target pathogen by generating a second electrical signal.

13. The bioelectrical sensor of claim 12, wherein the reaction element and the second reaction element are spaced apart from one another in the reaction chamber such that the fluid comes into contact with both the reaction element and the second reaction element as it flows through the reaction chamber.

14. The bioelectrical sensor of claim 1, wherein the bioelectrical sensor is attachable to and detachable from a bioelectrical sensor device, such that the bioelectrical sensor is in fluid communication with the bioelectrical sensor device when attached thereto.

15. The bioelectrical sensor of claim 1, wherein the first organism is synthetic.

16. A bioelectrical sensor system for identifying one or more pathogens in a fluid sample, the system comprising:

a loading port for loading a fluid sample into the system;

a pump for directing fluid flow through the system;

a substrate;

a bioelectrical sensor disposed on the substrate, the sensor comprising:

a reaction chamber to receive and emit fluid; and a reaction element disposed within the reaction chamber, wherein the reaction element comprises a first organism of a first species to detect a target pathogen, and comprises a second organism of a second species to generate an electrical signal, wherein the first organism detects the target pathogen by generating a voltage, wherein the second organism responds to the detecting of the target pathogen by generating the electrical signal based at least in part on the voltage generated by the first organism, and wherein the reaction element comprises a set of outer layers and an inner region disposed between the set of outer layers, the inner region is a hollow region and the second organism flows freely in a fluid in the inner region, and the reaction element allows ions released in response to the detection of the target pathogen by the first organism to travel from the set of outer layers to the inner region;

a signal channel to transmit the generated electrical signal; and a computing device to receive from the signal channel the generated electrical signal and identify, based at least in part on receiving the generated electrical signal from the signal channel, the first pathogen in the fluid sample.

17. The bioelectrical sensor system of claim 16, wherein the pump is a peristaltic pump, and wherein the pump is to generate cross-directional fluid flow through the reaction chamber.

18. The bioelectrical sensor system of claim 16, wherein the bioelectrical sensor is removable from the substrate, and wherein the substrate is reusable.

19. The bioelectrical sensor system of claim 16, wherein the signal channel comprises a wire to pass the generated electrical signal from the first reaction element to the computing device.

20. The bioelectrical sensor system of claim 16, wherein the computing device is disposed on the substrate.

21. The bioelectrical sensor system of claim 16, wherein the computing device is to identify the first pathogen in the fluid sample by mapping the received signal to the first pathogen.

22. The bioelectrical sensor system of claim 16, wherein the computing device is to, upon identifying the first pathogen in the fluid sample, generate an automated alert comprising information about the first pathogen.

23. The bioelectrical sensor system of claim 16, wherein the system is to provide the identification of the first pathogen in the fluid sample in less than 15 minutes from a time at which the fluid sample is loaded into the system to a time at which the first pathogen in the fluid sample is identified.

* * * * *